(12) United States Patent
Climo et al.

(10) Patent No.: US 7,122,514 B2
(45) Date of Patent: Oct. 17, 2006

(54) COMPOSITIONS AND METHODS FOR TREATMENT OF STAPHYLOCOCCAL INFECTION WHILE SUPPRESSING FORMATION OF ANTIBIOTIC-RESISTANT STRAINS

(75) Inventors: Michael Climo, Richmond, VA (US); Ellen Murphy, Bronx, NY (US); Gordon Archer, Richmond, VA (US)

(73) Assignee: Nutrition 21, Inc., Purchase, NY (US)

( * ) Notice: Subject to any disclaimer, the term of this patent is extended or adjusted under 35 U.S.C. 154(b) by 464 days.

(21) Appl. No.: 10/414,566

(22) Filed: Apr. 16, 2003

(65) Prior Publication Data

US 2003/0199432 A1 Oct. 23, 2003

Related U.S. Application Data

(62) Division of application No. 09/263,776, filed on Mar. 5, 1999, now Pat. No. 6,569,830.

(51) Int. Cl.
*A61K 38/00* (2006.01)
*A61K 38/16* (2006.01)
*A61K 38/48* (2006.01)

(52) U.S. Cl. .................. 514/2; 424/94.63; 435/183; 435/220

(58) Field of Classification Search .................. 514/2, 514/37; 435/183, 220; 424/363, 34.63
See application file for complete search history.

(56) References Cited

U.S. PATENT DOCUMENTS

| | | | |
|---|---|---|---|
| 3,278,378 | A | 10/1966 | Schindler et al. |
| 3,398,056 | A | 8/1968 | Zygmunt et al. |
| 3,594,284 | A | 7/1971 | Zygmunt et al. |
| 4,931,390 | A | 6/1990 | Recsei |
| 5,760,026 | A | 6/1998 | Blackburn et al. |
| 5,858,962 | A | 1/1999 | Blackburn et al. |
| 6,028,051 | A | 2/2000 | Climo et al. |

OTHER PUBLICATIONS

Craven et al. J. Vet. Pharmacol. Therap, 221-226, 1980.*
The Staphylococci in Human Disease. Chapter 26. pp. 583-595: Henry F. Chambers. "Parenteral Antibiotics for the Treatment of Bacteremia and Other Serious Staphylococcal Infections".
Diagn Microbiol Infect. Dis., 1993; 17:265-70. Polak, et al., "In Vitro Activity of Recombinant Lysostaphin-Antibiotic Combinations Toward Methicillin-Resistant *Staphylococcus aureus*".
The Staphylococci in Human Disease. Chapter 6 (part 2). pp. 158-174, Brigitte Berger-Bachi. Resistance Not Mediated By β-Lactamase (Methicillin Resistance).
FEMS Microbiology Letters. 153 (1997) pp. 261-264, Tschierske et al., "Lif. the Lysostaphin Immunity Factor. Complements Femβ in Staphylococcal Peptidoglycan Interpeptide Bridge Formation".
Applied and Environment Microbiology, Apr. 1995. pp. 1475-1479. DeHart et al., "The Lystostaphin Endopeptidase Resistance Gene (cpr) Specifies Modification of Peptidoglycan Cross Bridges in *Staphylococcus simulans* and *Staphylococcus aureus*".
Journal of Bacteriology. Jan. 1997. pp. 9-16. Stranden et al., "Cell Wall Monoglycine Cross-Bridges and Methicillin Hypersusceptibility in a Femβ Null Mutant of Methicillin-Resistant *Staphylococcus aureus*".
Canadian Journal of Microbiology, vol. 13 (1967). pp. 845-853. Zygmunt et al., "Lytic Action of Lysostaphin on Susceptible and Resistant Strains of *Staphylococcus aureus*".
Journal of Bacteriology, Dec. 1997. pp. 7573-7576. No. 23. Ehlert et al., "Specificities of FemA and Femβ for Different Glycine Residues: Femβ Cannot Substitute for FemA in Staphylococcal Peptidoglycan Pentaglycine Side Chain Formation".
Lystostaphin-Methicillin Therapy. vol. 41. Aug. 1968. pp. 62-68. Goodman et al., "Lysostaphin: An Anzymatic Approach to Staphylococcal Disease".
Yale Journal of Biology and Medicine. vol. 39. Feb. 1967. pp. 230-244. Schaffner et al., "Lysostaphin: An Enzymatic Approach to Staphylococcal Disease".
Kessler et al., "Secreted LasA of *Pseudomonas* aeruginosa Is a Staphylolytic Protease". Journal of Biological Chemistry. vol. 268. No. 10. pp. 7503-7508 (1993).
Li et al., "Purification. Staphylolytic Activity. and Cleavage Sites of α-Lytic Protease from *Achromobacter lyticus*". The Journal of Biological Chemistry. vol. 122. No. 4, pp. 772-778 (1997).
Oldham et al., "Lysostaphin: Use of a Recombinant Bactericidal Enzyme as a Mastitis Therapeutic"., J. Diary of Sci., 74:4175-82 (1991).
Martin et al., "The Selective Activity of Lysotaphin in vivo". The Journal of Laboratory and Clinical Medicine. vol. 70. No. 1, pp. 1-8 (Jul. 1967).
Martin et al., "The Reacquisition of Staphylococci by Treated Carriers: A Demonstration of Bacterial Interference". J. Lab. Clin. Med., vol. 71. No. 5, pp. 791-797 (May 1968).
Harrison et al., "Therapeutic Activity of Lysostaphin in Experimental Staphylococcal Infections". Canadian Journal of Microbiology. vol. 13. pp. 93-97 (1967).
Schuhardt et al., "Lysostaphin Therapy in Mice Infected with *Staphylococcus aureus*." J. Bacteriol., vol. 88. No. 1064. pp. 815-816.
Stark et al., Systemic Lysostaphin Man-Apparent Antimicrobial Activity in A Neutropenic Patient. The New England Journal of Medicine. pp. 239-240 (Aug. 1974).
Goldberg et al., "Studies in Experimental Staphylococcal Endocarditis in Dogs. VI. Treatment in Lysostaphin". Antimicrobial Agents and Chemotherapy, pp. 45-53 (1967).
Quickel Jr. et al., "Efficacy and Safety of Topical Lysostaphin Treatment of Persistent Nasal Carriage of *Staphylococcus aureus*", Applied Microbiology, pp. 446-450 (Sep. 1971).
Harrison et al., "Lysostaphin in Experimental Renal Infections". Journal of Bacteriology. pp. 520-524. (Feb. 1967).

* cited by examiner

*Primary Examiner*—Michael Borin
(74) *Attorney, Agent, or Firm*—Merchant & Gould, P.C.; Steven B. Kelber

(57) ABSTRACT

Co-administration of a lysostaphin or other anti-staphylococcal agent which cleaves cross-links of peptidoglycans of *staphylococci* cell walls such as lysostaphin and an antibiotic effective against *staphylococci* due to antibiotic activity mediated by cell-wall activity is effective against staphylococcal infection, even *staphylococci* that may be resistant to one or other of lysostaphin or the cell-wall active antibiotic. Co-administration simultaneously suppresses the generation of antibiotic-resistant mutant strains. Effective cell-wall active antibiotics include β-lactams and glycopeptides.

7 Claims, No Drawings

COMPOSITIONS AND METHODS FOR TREATMENT OF STAPHYLOCOCCAL INFECTION WHILE SUPPRESSING FORMATION OF ANTIBIOTIC-RESISTANT STRAINS

This application is a Division of application Ser. No. 09/263,776 Filed on Mar. 5, 1999 now U.S. Pat. No. 6,569,830.

BACKGROUND OF THE INVENTION

1. Field of the Invention

This invention pertains to a method of treating staphylococcal infection in mammals, including humans. The method involves the simultaneous administration of a lysostaphin or other agent which attacks the glycine-containing peptide cross-links of the cell wall peptidoglycan found in *staphylococci* and an antibiotic, the antibiotic properties of which are mediated by its ability to affect the cell wall of the target staphylococci. This combined administration is effective in treating the staphylococcal infection, and at the same time suppresses the formation of strains resistant to lysostaphin or other peptidoglycan active agent.

2. Background of the Prior Art

Lysostaphin is a bacteriocin secreted by a staphylococcal strain isolated and originally named *Staphylococcus staphylolyticus* (now *S. simulans*). The production of lysostaphin is described in U.S. Pat. No. 3,278,378. Lysostaphin is an endopeptidase which cleaves the polyglycine cross-links of the peptidoglycan found in the cell walls of staphylococci. U.S. Pat. Nos. 3,398,056 and 3,594,284 describe improvements to culture medium and inoculation techniques for the production of lysostaphin.

The gene for lysostaphin from *S. simulans* has been sequenced and cloned, U.S. Pat. No. 4,931,390. Lysostaphin for use as a laboratory reagent has been produced by fermentation of a non-pathogenic recombinant strain of *B. sphaericus*, from which it is readily purified. The cloning and sequencing of the lysostaphin gene permits the isolation of variant enzymes that have properties similar to or different from those of wild type lysostaphin. One such altered enzyme, bearing a single amino acid change, has been characterized and shown to have potent anti-staphylococcal activity both in vitro and in an animal infection model. U.S. patent application Ser. No. 09/120,030, filed Jul. 21, 1998 and incorporated herein by reference. Other lysostaphin analogues, including naturally occurring enzymes of this type have been established as potent agents capable of addressing difficult to treat bacterial diseases caused by staphylococcal infection. Other peptidases with related activity are known. Thus lasA protease and achromopeptidase, reported in Kessler, et al., J. Biol. Chem. 268:7503–08 (1993) and Li et al., J. Biochem. 122:772–778 (1997), respectively, have anti-staphylococcal activity based on their digestion of glycine-containing cross-links in the peptidoglycan cell wall component. These agents may be used in this invention in place of lysostaphin.

The development of lysostaphin as an effective antibiotic to treat staphylococcal infection has been plagued, however, by a problem that is universal for antibiotic administration—the increasing development of antibiotic-resistant strains of mutant staphylococci. Already, a wide variety of staphylococcal infections resistant to various antibiotics that were previously the treatment of choice, including methicillin (methicillin resistant *S. aureus* are referred to as MRSA) and vancomycin-resistant strains (referred to as VISA) have been identified. Resistance to a wide variety of other antibiotics, not exhibited by sensitive staphylococci, has been noted as well. MRSA, as well as strains resistant to other antibiotics, are discussed at length in Stranden, et al., J. Bacteriology 179(1):9–16 (1997). Further difficulties are encountered in that MRSA tend to accumulate a variety of other resistances as well. Multiresistant MRSA are typically treated with vancomycin, *The Staphylococci In Human Diseases*, 158–174 (Grossley, et al., editors 1997). Vancomycin itself may be toxic. Additionally, vancomycin resistance has recently been detected in *staphylococci* infections.

The problem posed by the continuing development of antibiotic-resistant infectious agents, such as staphylococci, is more than the difficulty involved in treating any individual patient. Popular press, as well as scientific journals, have noted the alarming increase in the generation of resistant strains, due in part to indiscriminate use or over-use of antibiotics. Each time an individual is treated with an antibiotic, whether needlessly or reasonably, the chance that a strain resistant to that particular treatment will arise is increased. Resistant strains of *staphylococci* have become endemic in many hospitals and pose a life-threatening danger to patients already debilitated by other ailments who become infected after admission to those hospitals.

Numerous articles have noted the development of resistance to either lysostaphin or β-lactams, such as methicillin, and the relationship there between. Thus, DeHart, et al., Applied Environmental Microbiology 61, 1475–1479 (1995) noted the development of mutant *S. aureus* recombinant cells that were resistant to lysostaphin, but susceptible to methicillin. Similar phenomenon are reported by Zygmunt, et al., Can. J. Microbio. 13,845–852 (1966), Polak. et al., Diagn. Microbiol. Infet. Dis. 17:265–270 (1993) and Dickson, et al., Yale J. Bio. Med. 41:62–67 (1968). Each of these references, as well as later reports such as Ehlert, J. Bacteriology, 179:7573–7576 (1997) note that staphylococci that develop resistance to lysostaphin, either spontaneously or through induced recombination, become susceptible to methicillin treatment, and vice-versa. In all of these references, the uniform suggestion is to follow a course of administration of lysostaphin, even a short one, with administration of methicillin.

U.S. Pat. No. 5,760,026, commonly assigned herewith, employs a specific method for treating mastitis, by intramammary infusion of lysostaphin. The patent reports, Table ID and elsewhere, that a synergistic result is predicted when combining lysostaphin and a β-lactam to treat mastitis, based on an in vitro assay. The bovine mastitis model is not predictive of in vivo administration of antibiotics, and the synergistic effects reported in U.S. Pat. No. 5,760,026 have not been substantiated in an environment or model that would be reflective of in vivo administration to a mammal such as a human.

Those of skill in the art will be aware that there are a wide variety of staphylococcal strains. Many are resistant to conventional antibiotics, unlike sensitive strains. *S. aureus* strains are recognized as highly virulent and the most common single cause of serious systemic infections. Coagulase-negative staphylococcal species, although generally less invasive than *S. aureus*, are now responsible for a significant incidence of infections; particulary among debilitated or immunocompromised patients. As an example of such infection, one may point to endocarditis consequent to heart valve replacement. This is but one of a variety of intractable staphylococcal infections which are increasing due to the widespread use of antibiotics.

Accordingly, it remains an object of those of ordinary skill in the art to develop a method whereby even resistant staphylococcal infections in mammals, including humans, may be effectively treated by the administration of antibiotics. Desirably, this method is developed so as suppress the formation of strains resistant to the antibiotics used.

SUMMARY OF THE INVENTION

The above goals, and others made clear by the discussions set forth below, are achieved by the simultaneous administration of an anti-staphylococcal agent, such as lysostaphin or other agent whose activity is mediated by cleavage of glycine-containing cross-links in the staphylococcal cell wall peptidoglycan and an antibiotic or antimicrobial agent whose activity is mediated by its ability to affect the cell wall of staphylococci. These cell-wall active agents include β-lactams and glycopeptides. Preferably, the cell-wall active antibiotic is a β-lactam.

There is no evidence of any synergistic effect achieved through the simultaneous administration of an anti-staphyloccocal agent whose activity is mediated by cleavage of glycine-containing cross-links and a cell-wall active antibiotic in a model, in vitro or in vivo, that is predictive of benefit for in vivo administration of antibiotics in a mammal. Indeed, those of ordinary skill in the art will recognize that for resistant staphylococci, such as MRSA, the administration of methicillin is not therapeutically effective in any amount. Surprisingly, Applicants have discovered that the combined administration of an anti-staphyloccocal agent whose activity is mediated by cleavage of glycine-containing cross-links such as lysostaphin and the cell-wall active antibiotic not only effectively treats the infection, but suppresses the formation of *staphylococci* having resistance to the anti-staphylococcal agent whose activity is mediated by cleavage of glycine-containing cross-links.

While Applicants do not wish to be bound by this explanation, it appears that the spontaneous mutation commonly effective in conferring lysostaphin resistance in *staphylococci* renders the same highly susceptible to a cell-wall active antibiotic, such as methicillin. This is true even where the organism starts out as methicillin resistant. Simultaneous administration of both appears to be uniformly effective in simultaneously eradicating the infection and suppressing the generation of new resistant strains. Specifically, anti-staphylococcal agents like lysostaphin cleave glycine-containing cross-links. The mutation conferring resistance to this attack renders previously resistant strains sensitive to cell wall active antibiotics.

DETAILED DESCRIPTION OF THE INVENTION

This invention involves the administration of a pharmaceutical composition effective in the treatment of staphylococcal infection, which composition comprises at least two active agents, one an agent like lysostaphin which cleaves the glycine-containing cross-links of the cell wall peptidoglycans of staphylococci, the other a cell-wall active antibiotic. By lysostaphin it is intended to refer herein to any enzyme, including lysostaphin wild type, a mutant or variant, or any recombinant or related enzyme that retains proteolytic activity against glycine-containing cross-links in the cell wall peptidoglycan of staphylococci. Variants may be generated by post-translational processing of the protein (either by enzymes present in a producer strain or by means of enzymes or reagents introduced at any stage of the process) or by mutation of the structural gene. Mutations may include site-deletion, insertion, domain removal and replacement mutations. They may be recombinantly expressed, or otherwise. Other anti-staphylococcal active agents acting by cleavage of the glycine-containing peptidoglycan cross-links include lasA protease and achromopeptidase. Such anti-staphylococcal agents which affect the peptidoglycan cross-links are embraced by the invention, but exemplified herein by reference to lysostaphin.

Cell-wall active antibiotics include β-lactams and glycopeptides. β-lactams are preferred. Suitable β-lactams include, but are not limited to, penicillins, such as penicillin, nafcillin, oxacillin, methicillin, amoxicillin and cloxacillin. Other β-lactams include cephalosporins and carbapenems. Representative cephalosporins include cephalothin, cefazolin, cefamandole, ceftazidime and others. Suitable carbapenems include imepenem and meropenem.

Suitable glycopeptides include vancomycin, teicoplanin and ramoplanin.

These two agents can be combined with further agents, adjuvants and the like, but are effectively administered in a pharmaceutically acceptable carrier. Administration is typically systemic, and may be intravenous (IV), intramuscular (IM), subcutaneous (SC), intraperitoneal (IP), intrathecal or topical. No synergistic effect of combining lysostaphin and a β-lactam or glycopeptide or cell-wall active antibiotic has been noted in a model predictive of in vivo mammalian administration. Accordingly, each agent of the effective combination must be administered in a therapeutically effective amount. It is to be noted, in this regard, that the amount to be administered is that which is therapeutically effective when the lysostaphin and cell-wall active agent are administered together. Those of skill in the art will of course recognize that there is no therapeutically effective amount for, e.g.,methicillin if the staphylococcal infection is an MRSA infection. Nonetheless, administration of therapeutic amounts of methicillin as determined against non-MRSA, combined with an amount of lysostaphin effective against *staphylococci* that are not lysostaphin-resistant will effectively treat staphylococcal infections even where the infection is resistant to one or other antibiotic. Accordingly, applicants have referred herein to "therapeutically effective amounts" to mean amounts effective to therapeutically treat sensitive *S. aureus* infection. This simultaneous administration, as opposed to sequential administration typified by the prior art, also surprisingly results in the suppression of strains resistant against either antibiotic, or their combination.

Any of a wide variety of pharmaceutically acceptable carriers and diluents, typically buffered, may be used. Appropriate pharmaceutical carriers are known to those of skill in the art. The formulations of this invention comprise a therapeutic amount of lysostaphin and a therapeutic amount of a cell-wall active antibiotic, such that when co-administered, the staphylococcal infection, either *S. aureus* or coagulase negative staphylococci, is treated, while the generation of resistant strains is suppressed. Other active agents that do not interfere with the activity of the two antibiotics may be co-administered.

Therapeutic values will range substantially given the nature of the staphylococcal infection, the individual, and the antibiotic being used in conjunction with lysostaphin. Representative values for anti-staphyloccocal active agents such as lysostaphin, range from approximately 15–150 mg/kg body weight/day for human administration, with a preferred range of 25–100 mg/kg/day. Values for β-lactams based on nafcillin range from 50–250 mg/kg/day, with a preferred range of 100–200 mg/kg/day and glycopeptides like vancomycin are administered over a range of 10–75 mg/kg/day, with a preferred range of 15–50 mg/kg/day.

The administration course is not substantially different from that currently administered in single antibiotic treatments, and can range from 7–28 days, although typically, courses of 7–21 days are employed, and effective in treating a wide variety of staphylococcal infections.

EXAMPLES

To compare the development of resistant strains, growth curves for three methicillin resistant staphylococcal strains were obtained for in vitro growth in Mueller Hinton Broth.

Growth curves were completed in Mueller Hinton Broth (50 ml) in glass erlenmeyer flasks. Flasks were inoculated with 100 µl of an overnight growth adjusted to 0.5 Macfarland to yield a starting concentration of approximately $10^5$–$10^6$ CFU/ml. Growth curves were done in the presence of lysostaphin, lysostaphin and oxacillin (1 µg/ml) or no antibiotics (controls). Absorbance at OD 600 was recorded at 0, 2, 4, 6 and 24 hours. At 24 hours flasks were plated on MHA, MHA with lysostaphin (6 µg/ml) and MHA with oxacillin (6 µg/ml) in order to screen for resistant mutants. Three methicillin resistant *Staphylococcus aureus* strains were tested: 272855, 450M and Mu3.

Growth following 24 hour incubation with lysostaphin (0.0625 µg/ml), lysostaphin (0.0625 µg/ml) and oxacillin (1 µg/ml), and no antibiotics, was recorded.

The data generated led to the following conclusions:
1. The addition of oxacillin to lysostaphin led to significant suppression of growth for all three strains.
2. The presence of oxacillin suppressed the expression of lysostaphin resistance among all three strains.

In order to demonstrate the effectiveness of the claimed invention, certain experiments were conducted. Checkerboard susceptibility testing was conducted to determine whether simultaneous administration of lysostaphin and oxacillin (a β-lactam) would be effective in suppressing the development of resistance. Oxacillin concentrations varied between 0.0156 µg/ml and 1 µg/ml. Lysostaphin concentrations varied between 0.00048 and 0.9 µg/ml. Four strains were tested for evidence of synergy between lysostaphin and oxacillin; 27619, Col, 27227 and VA348. There was no evidence of synergy or antagonism over the concentration range tested. The MIC of lysostaphin was unchanged in the presence of oxacillin in concentrations up to 1 µg/ml for all strains tested. The overnight growth of strains in the presence of lysostaphin and oxacillin was examined. Four strains were grown overnight in drug free media (MHB), MHB with 0.1 µg/ml of lysostaphin, MHB with lysostaphin 0.1 µg/ml and oxacillin 1 µg/ml, and MHB with oxacillin 1 µg/ml. The four strains tested included 450M, Col, and their lysostaphin resistant mutants 450 M lyso and Col lyso. The results are reflected in Table 1.

The same unpredicted result has been demonstrated through in vivo experiments based on the widely accepted rabbit model of aortic valve endoearditis, predictive of in vivo administration to humans. When administered to staphylococcal infected rabbits at low doses (1 mg/kg bid, as compared with a minimum value of 5 mg/kg tid for sterilization) lysostaphin, as representative of anti-staphylococcal agents acting by cleavage of the glycine-containing cross-links, resulted in recovery of a number of resistant colonies, with high counts in vegetations and kidneys, while the same dosage together with nafcillin (a β-lactam) gave sterile kidneys, some sterile vegetations, and no resistant strains recovered. The simultaneous treatment of staphylococcal infection with suppression of resistant strain formation is an exciting and widely useful invention nowhere predicted in the art. This invention offers the possibility of treating staphylococcal infections while suppressing the generation of strains resistant to any or all active agents administered.

The inventive compositions and methods of this application have been disclosed generically, and by reference to specific example, examples are not intended to be limiting unless so indicated, and variations will occur to those of ordinary skill in the art without the exercise of inventive faculty. In particular, variations in the identity of the cell-wall active antibiotic to be co-administered with an anti-staphylococcal agent acting by cleavage of the glycine-containing cross-links, as well as various recombinant and mutant variants thereof, carriers and concentrations will occur to those of skill in the art without the exercise of inventive faculty, and remain within the scope of the invention, unless specifically excluded by the claims set forth below.

What is claimed is:

1. A composition comprising lysostaphin and a glycopeptide antibiotic;

wherein the weight ratio of lysostaphin to glycopeptide antibiotic in the composition ranges from 0.2:1 to 15:1.

2. The composition of claim 1, wherein the glycopeptide antibiotic is selected from the group consisting of vancomycin, teicoplanin and ramoplanin.

3. The composition of claim 1, wherein the glycopeptide antibiotic is vancomycin.

4. The composition of claim 1, further comprising a pharmaceutically acceptable carrier.

5. The composition of claim 1, wherein the composition is in a form suitable for intravenous, intramuscular, subcutaneous, intraperitoneal, intrathecal or topical administration.

TABLE 1

|  | Growth in the presence of | | | |
|---|---|---|---|---|
| Isolates | MHB | lysostaphin 0.1 µg/ml | oxacillin µg/ml | Lyso + oxacillin |
| 450 M | + | + | + | − |
| 450 M lyso | + | + | − | − |
| Col | + | + | + | − |
| Col lyso | + | + | − | − |

6. The composition of claim 1, wherein the weight ratio of lysostaphin to glycopeptide antibiotic in the composition ranges from 0.5:1 to 6.67:1.

7. The composition of claim 1, wherein the composition, when administered to a human subject for a period of time sufficient to eradicate said infection, suppresses formation of staphylococcal strains resistant to the lysostaphin and the cell-wall active antibiotic.

* * * * *

UNITED STATES PATENT AND TRADEMARK OFFICE
CERTIFICATE OF CORRECTION

PATENT NO. : 7,122,514 B2
APPLICATION NO. : 10/414566
DATED : October 17, 2006
INVENTOR(S) : Michael Climo, et al.

It is certified that error appears in the above-identified patent and that said Letters Patent is hereby corrected as shown below:

Title page in the Abstract, Column 2, line 3:
    "*staphylococci*" should read --staphylococci--.

Title page in the Abstract, Column 2, line 4.
    "*staphylococci*" should read --staphylococci--.

Title page in the Abstract, Column 2, line 6:
    "*staphylococci*" should read --staphylococci--.

Column 1, line 19:
    "*staphylococci*" should read --staphylococci--.

Column 1, line 45:
    "in vitro" should read --*in vitro*--.

Colunm 1, line 52:
    "lasA" should read --*lasA*--.

Column 2, line 11:
    "*staphylococci*" should read --staphylococci--.

Column 2, line 21:
    "*staphylococci*" should read --staphylococci--.

Column 2, line 49:
    "in vitro" should read --*in vitro*--.

Column 2, line 50:
    "in vivo" should read --*in vivo*--.

Column 2, line 53:
    "in vivo" should read --*in vivo*--.

Column 3, line 24:
    "in vitro or in vivo" should read --*in vitro or in vivo*--.

Column 3, line 25:
    "in vivo" should read --*in vivo*--.

Column 3, line 30:
    "anti-staphyloccocal" should read --anti-staphylococcal--.

UNITED STATES PATENT AND TRADEMARK OFFICE
CERTIFICATE OF CORRECTION

PATENT NO. : 7,122,514 B2
APPLICATION NO. : 10/414566
DATED : October 17, 2006
INVENTOR(S) : Michael Climo, et al.

It is certified that error appears in the above-identified patent and that said Letters Patent is hereby corrected as shown below:

Column 3, line 34:
"*staphylococci*" should read --staphylococci--.

Column 3, lines 39-40:
"*staphylococci*" should read --staphylococci--.

Column 4, line 6:
"lasA" should read --*lasA*--.

Column 4, line 27:
"in vivo" should read --*in vivo*--.

Column 4, line 39:
"*staphylococci*" should read --staphylococci--.

Column 4, line 63:
"anti-staphyloccocal" should read --anti-staphylococcal--.

Column 5, line 14:
"in vitro" should read --*in vitro*--.

Column 6, line 2:
"in vivo" should read --*in vivo*--.

Column 6, lines 3-4:
"in vivo" should read --*in vivo*--.

Signed and Sealed this

Third Day of April, 2007

JON W. DUDAS
*Director of the United States Patent and Trademark Office*